(12) United States Patent
Grossman

(10) Patent No.: US 6,215,010 B1
(45) Date of Patent: Apr. 10, 2001

(54) SYNTHESIS OF ORGANOTIN OXIDES

(75) Inventor: Richard F. Grossman, Wilmington, DE (US)

(73) Assignee: Hammond Group, Inc., IN (US)

( * ) Notice: Subject to any disclaimer, the term of this patent is extended or adjusted under 35 U.S.C. 154(b) by 0 days.

(21) Appl. No.: 09/631,025

(22) Filed: Aug. 2, 2000

(51) Int. Cl.⁷ .................................................. C07F 7/22
(52) U.S. Cl. ................................................... 556/88
(58) Field of Search ................................. 556/88

(56) References Cited

U.S. PATENT DOCUMENTS

| | | | |
|---|---|---|---|
| 3,376,329 | * 4/1968 | Kobetz et al. | 260/429.7 |
| 3,390,159 | * 6/1968 | Katsumura et al. | 260/429.7 |
| 3,448,130 | * 6/1969 | Oakes et al. | 260/429.7 |
| 3,466,311 | * 9/1969 | Mizuno et al. | 260/429.7 |
| 3,493,592 | * 2/1970 | Shapiro et al. | 260/429.7 |
| 3,711,524 | * 1/1973 | Leebrick et al. | 260/429.7 |
| 3,813,424 | * 5/1974 | Hayashi et al. | 260/429.7 |
| 4,968,823 | * 11/1990 | Kiyama et al. | 556/88 |

* cited by examiner

*Primary Examiner*—Porfirio Nazario-Gonzalez
(74) *Attorney, Agent, or Firm*—Wood, Herron & Evans, L.L.P.

(57) ABSTRACT

Organotin oxides are synthesized by reacting powdered tin metal with an alcohol at elevated temperatures on the order of about 200–400° C. Dialkyltin oxides are produced in quantitative yields according to the method.

14 Claims, No Drawings

SYNTHESIS OF ORGANOTIN OXIDES

FIELD OF THE INVENTION

This invention relates to the synthesis of organotin oxides which are useful as intermediates in the preparation of organotin stabilizers.

BACKGROUND OF THE INVENTION

Organometallics, compounds containing carbon-metal bonds, tend to be compatible with polar polymers such as PVC. Most organometallics have disadvantages: toxicity (alkyl lead, zinc and mercury compounds), violent reactivity to air or water (organo-aluminum and titanium compounds), or high reactivity towards polar substrates (silanes). An exception is the case of mono- and dialkyltin derivatives. In a typical stabilizer, tin, in the (IV) oxidation state, is covalently bound to either one or two alkyl groups, and, correspondingly, either two or three reactive ligands. The latter are capable both of displacing labile chlorine and scavenging HCl. The resultant mono- and diorganotin compounds form a group of valuable stabilizers, principally for rigid PVC, but with some flexible PVC use. The generalized stabilizer formula is $R_2SnX_2$ or $R_2SnX_3$.

In the first generation of tin stabilizers to appear in the late 1930's in the United States, the R-group used in the above general formula was n-butyl, because of the availability and relative low cost of n-butyl chloride, and its suitability in the Grignard reaction with magnesium, as follows:

$$R\text{—}Cl+Mg \rightarrow R\text{—}Mg\text{—}Cl \quad (1)$$

The resultant Grignard reagent reacts rapidly with tin halides, replacing chloride with the R-group. In practice, tin tetrachloride was converted to tetrabutyltin, originally with butylmagnesium chloride, more recently with the corresponding aluminum trialkyl.

$$SnCl_4+4R\text{—}MgCl \rightarrow R_4Sn+4MgCl_2 \quad (2)$$

$$3SnCl_4+AlR_3 \rightarrow 3R_4Sn+4AlCl_3 \quad (3)$$

The resultant tetraalkyltin is then reacted further with tin tetrachloride, causing disproportionation into a range of alkyltin chlorides, which are separated by fractional distillation.

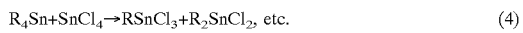

$$R_4Sn+SnCl_4 \rightarrow RSnCl_3+R_2SnCl_2, \text{ etc.} \quad (4)$$

The disproportionation process and fractionation can be controlled to yield mixtures of almost entirely mono and diorganotin chlorides, ranging from an equilibrium 65/35 di/mono ratio to pure mono- or di-, depending on reaction conditions. These intermediates are then reacted with carboxylic acids or with ligands containing mercaptan groups to yield actual stabilizers.

Dimethyltin dichloride intermediate is now produced directly from tin and methyl chloride.

$$Sn+2CH_3Cl \rightarrow (CH_3)SnCl_3 \quad (5)$$

Similarly, monomethyltin trichloride is synthesized from stannous chloride:

$$SnCl_2+CH_3Cl \rightarrow CH_3SnCl_3 \quad (6)$$

These methods are cost effective and, in addition, directly yield intermediates without the need for fractional distillation of a mixture. However, these alkyltin chloride intermediates are corrosive, require glass lined reactors, and have undesirably toxic properties.

It would be very advantageous to eliminate the need to produce alkyltin chloride intermediates in making organotin stabilizers. New methods are also desired for producing organotin compounds to overcome the disadvantages of known methods.

SUMMARY OF THE INVENTION

This invention is directed to a method of making organotin oxides. These organotin oxides have many uses including their use as intermediates in the preparation of tin stabilizers for polymer compositions, especially vinyl halide polymers.

The method involves preparation of dialkyltin oxides directly from tin powder and alcohols. Powdered tin metal is reacted with an alcohol at an elevated temperature, on the order of about 200–400° C. in the presence of an acidic catalyst to produce the desired alkyltin oxide.

The objectives and advantages of this invention will be understood with reference to the following detailed description and operating examples.

PREFERRED MODE AND DETAILED DESCRIPTION

The method of this invention is practiced by reacting powdered tin metal with a primary alcohol in the presence of an acidic catalyst at an elevated temperature. The powdered tin metal has a particle size range on the order of about 200 mesh or finer, preferably from about 300 to about 400 mesh. A number of primary alcohols may be used in the invention including methanol, butanol, and octanol. A Lewis acid catalyst is preferred in order to obtain quantitative yields in a shorter reaction period. The yields with primary alcohols go down as the molecular weight increases. A number of different acidic catalysts may be employed including anhydrous stannous chloride, anhydrous aluminum Chloride or Boron trifluoride. The temperatures of the reaction will vary depending upon the reactants; however, usually temperatures on the order of about 200 to about 400° C. are employed. The alkyltin oxide is collected upon cooling at temperatures below 0° C., preferably −20° C. to −60° C., and under vacuum.

The following examples illustrate the practice of the invention, but are not considered to be limiting the broader aspects of the inventive method.

EXAMPLE 1

A vacuum system was set up with the following components: a quartz tube that could be heated in a muffle furnace, leading to a cold trap into which product could be vacuum distilled. A quartz boat in the tube contained 12 g (circa 0.1 mol) 325 mesh tin powder and 0.2 g anhydrous stannous chloride. Air was evacuated from the system and the tin powder heated to 280° C., as determined by an infrared thermometer. The cold trap was cooled to −20° C. using an ice/acetone bath. A second cold trap, nearer to the high vacuum source, was cooled to −65° C. with dry ice/acetone. 7 g anhydrous methanol was injected slowly into the system so as to pass above the tin powder. A white solid collected in the ice/acetone cooled trap, and traces of water in the dry ice/acetone trap. In about 2 hours, 95+% of the tin powder was consumed. The yield was 15 g (91%) of dimethytin oxide, having an infrared spectrum identical to commercial product, as was the tin content (72%).

EXAMPLE 2

Example 1 was repeated using anhydrous aluminum chloride as the catalyst. A 93% yield of dimethyltin oxide was obtained. Use of anhydrous zinc chloride led to a yield of 90%. Without catalyst, the yield was 27% after 8 hours, 35% at 325° C. Without a Lewis acid catalyst, but with introduction of a 95/5 methanol/anhydrous HCl mixture, the yield was 76% after 4 hours, 80% at 325° C.

EXAMPLE 3

Example 1 was repeated using 15 g of n-butanol in place of methanol. 6 hours of reaction at 240° C. led to a 65% yield of dibutyltin oxide, having an infrared spectrum identical to a commercial sample. 24 hours at 240° C. led to a 71% yield. In both cases, the rest of the butanol was converted to 1-butene (with small amounts of rearrangement to 2-butene) as determined by gas chromatography, and traces of polybutene.

The above examples illustrate the method of this invention on the batch scale. In another form, the invention may be practiced by injecting finely powdered tin into a recirculating flash calciner having an air-free atmosphere containing the appropriate alcohol and means for trapping and quickly cooling the reaction product.

In view of the above description and examples, other variations of the method may be employed without departing from the scope of the invention as will be understood to a person of skill in the field.

What is claimed is:

1. A method of making a dialkyltin oxide comprising reacting powdered tin metal with an alcohol at an elevated temperature to produce the dialkyltin oxide.
2. The method of claim 1 wherein the reaction is conducted in the presence of a catalyst.
3. The method of claim 2 wherein the catalyst is a Lewis acid.
4. The method of claim 1 wherein the catalyst is selected from the group consisting of anhydrous stannous chloride and anhydrous aluminum chloride.
5. The method of claim 1 wherein the alcohol is selected from the group consisting of methanol, butanol and octanol.
6. The method of claim 1 conducted at a temperature on the order of about 200–400° C. in the absence of air.
7. The method of claim 1 wherein the particle size of the powdered tin metal is on the order of about 300 to about 400 mesh.
8. The method of claim 1 wherein the particle size is about 200 mesh or finer.
9. The method of claim 1 wherein the alcohol is introduced into the tin powder at the elevated temperature for reaction to produce the organotin oxide which is subsequently cooled and collected at a reduced temperature.
10. The method of claim 9 wherein the reduced temperature is below 0° C.
11. A method of making a dialkyltin oxide comprising
    reacting powdered tin metal having a particle size on the order of about 300 to about 400 mesh with an aliphatic primary alcohol to produce a dialkyltin oxide at a temperature on the order of about 200–400° C.
12. The method of claim 11 wherein a dialkyltin oxide is produced by reacting the tin metal with an alcohol from the group consisting of methanol, butanol and octanol in the presence of a Lewis acid catalyst and in the absence of air.
13. The method of claim 11 wherein the alcohol is methanol.
14. The method of claim 11 wherein the alcohol is butanol.

* * * * *